United States Patent [19]

Berger

[11] 4,270,273
[45] Jun. 2, 1981

[54] MEASURING INSTRUMENT

[75] Inventor: Brian E. Berger, Richmond, Va.

[73] Assignee: A. H. Robins Company, Inc., Richmond, Va.

[21] Appl. No.: 89,297

[22] Filed: Oct. 30, 1979

[51] Int. Cl.³ .............................................. B43L 9/08
[52] U.S. Cl. ................................... 33/150; 33/149 B; 33/192
[58] Field of Search ............... 33/149 R, 149 B, 192, 33/1 C, 150, 27 B

[56] References Cited

U.S. PATENT DOCUMENTS

| 61,926 | 2/1867 | Copeland | 33/192 |
| 723,720 | 3/1903 | Ostlund | 33/149 B |
| 1,201,342 | 10/1916 | Peck | 33/149 B |
| 1,303,471 | 5/1919 | Gross | 33/149 B |
| 1,710,414 | 4/1929 | Falletta | 33/149 B |
| 2,770,046 | 11/1956 | Wichmann | 33/192 X |
| 3,214,835 | 11/1965 | Barquero | 33/149 B |
| 4,030,486 | 6/1977 | Eastman | 33/1 C |

FOREIGN PATENT DOCUMENTS

| 40757 | 1/1910 | Austria | 33/192 |
| 160486 | 9/1957 | Sweden | 33/150 |

OTHER PUBLICATIONS

American Practical Navigator, N. Bowdetch, U.S. Govt. Printing Office, H.O. Pub. #9, pp. 845-847.

Primary Examiner—Harry N. Haroian
Attorney, Agent, or Firm—Burns, Doane, Swecker & Mathis

[57] ABSTRACT

A measuring instrument, preferably for determining the mean arterial blood pressure from a graph containing values of systolic pressure and diastolic pressure. The instrument comprises a compass having a pair of outer legs and a single intermediate leg disposed therebetween. The outer legs are arranged to enable the distance between outer ends thereof to be manually varied. A proportioning mechanism maintains an outer end of the intermediate leg at a constant ratio, preferably one-third, of the distance between the outer legs.

6 Claims, 2 Drawing Figures

MEASURING INSTRUMENT

BACKGROUND AND OBJECTS OF THE INVENTION

The present invention relates to instruments for measuring the distance between points on a planar surface, and especially to instruments for measuring mean arterial blood pressure from a polygraph chart or the like.

Current diagnostic practice for determining the mean arterial blood pressure of a patient involves sensing the patient's blood pressure and obtaining a visual readout thereof, such as by means of a polygraph chart, a "Z-fold" paper chart, or an oscilloscope screen. The values of systolic pressure and diastolic pressure are observed from the chart or screen and the value of the latter is subtracted from the former. The remainder produced by such subtraction is then multiplied by one-third and that one-third value is added to the value of the diastolic pressure to produce a sum which constitutes the mean arterial blood pressure.

It will be appreciated that the numerous measurements and calculations needed for such a determination are time consuming and create appreciable opportunity for error.

It is, therefore, an object of the present invention to minimize or obviate problems of the type discussed above.

It is another object of the invention to provide novel measuring methods and apparatus for obtaining a reading directly from a chart.

It is an additional object of the invention to enable the mean arterial blood pressure to be determined from a chart without the need for taking multiple readings from the chart or making calculations.

It is a further object of the invention to provide a measuring instrument which instantaneously determines the mean arterial blood pressure from a chart.

It is an additional object of the invention to provide such a measuring instrument which includes three adjustable legs, wherein an intermediate one of the legs remains disposed at a contact ratio between the two outer legs during adjustment of the legs.

It is yet another object of the invention to provide such an instrument which includes an adjustment screw extending between the outer legs and through the intermediate leg, wherein the portion of the screw extending through the intermediate leg has a pitch which is less than that of the screw portion extending through an adjustable one of the outer legs.

SUMMARY OF THE INVENTION

These objects are achieved by the present invention which involves a measuring instrument comprising first and second outer legs and a single intermediate leg disposed therebetween. The outer legs are arranged to enable the distance between outer ends thereof to be manually varied. A proportioning mechanism is provided for maintaining an outer end of the intermediate leg at a constant ratio of the distance between the outer legs.

When using the instrument to determine mean arterial blood pressure from a graph containing values of systolic pressure and diastolic pressure, the intermediate leg is maintained constantly at one-third the distance between the outer ends of the outer legs so that the instrument can measure the mean arterial blood pressure directly from the graph.

THE DRAWING

Other objects and advantages of the invention will become apparent from the following detailed description of a preferred embodiment thereof in connection with the accompanying drawings in which like numerals designate like elements, and in which:

FIG. 1 is a side elevational view of an instrument according to the present invention, and FIG. 2 is a chart from which a reading of mean arterial pressure can be directly read by the instrument.

DETAILED DESCRIPTION OF A PREFERRED EMBODIMENT OF THE INVENTION

Figure 1:
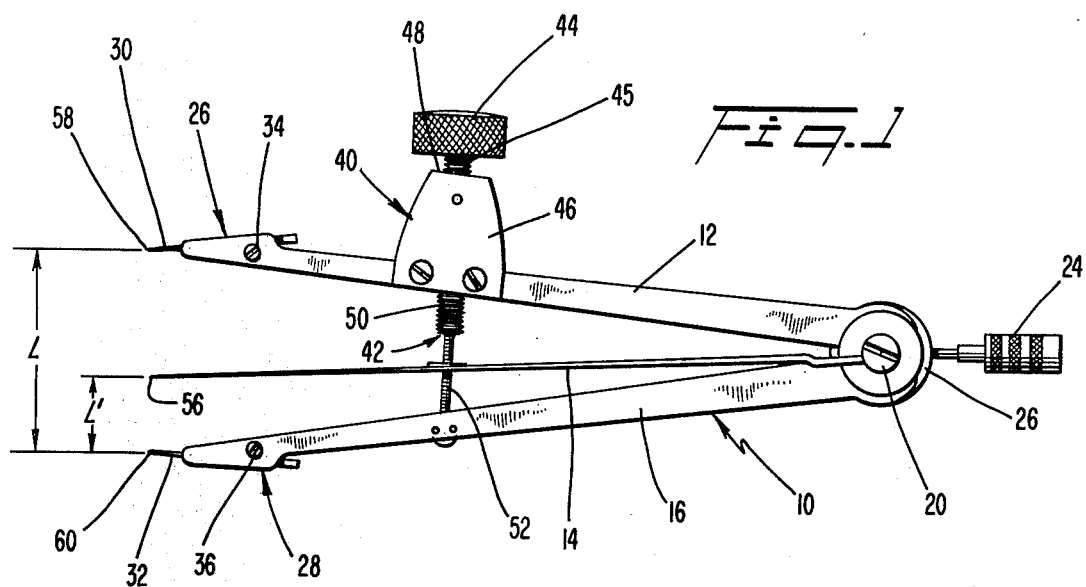

A measuring instrument 10 according to the present invention comprises a compass having three legs 12, 14, 16. Each of the legs includes an apertured upper mounting portion through which a pivot pin 20 extends, allowing each of the legs to swivel independently about a rotary axis defined by such pin 20.

A housing part 22 straddles the mounted portions of the legs. A support knob 24 is connected to a stationary washer 26 and enables the compass to be manually gripped.

Lower ends 26, 28 of the outside ones 12, 16 of the legs include pockets for adjustably receiving points 30, 32, respectively. Adjustment screws 34, 36 are mounted within the pockets for holding the points 30, 32 in adjusted positions.

An adjustment mechanism 40 is provided for simultaneously adjusting all three legs while automatically locating the intermediate one 14 of the legs at a constant ratio between the outside legs 12, 16.

The adjustment mechanism comprises a threaded proportioning screw 42 which extends through bores in each of the three legs 12, 14, 16. Fixedly attached to the screw is a manual control knob 44 to enable the screw to be manually rotated.

The bore within a first one 12 of the outer legs which receives the screw 42 is threaded, while the bore within the second outer leg 16 merely supports an end of the screw 42 for free rotation therein. In order to support that portion 45 of the screw which projects beyond the first leg 12, a flange 46 is provided which may contain a threaded aperture in its outer face 48.

The screw 42 is threadedly received in a threaded bore of the intermediate leg 14.

It will be appreciated, then, that upon rotation of the screw 42, both the first leg 12 and the intermediate leg 14 will each be displaced axially therealong due to the threaded engagement therebetween.

A first section 50 of the screw 42, which extends through the first outer leg 12, has a pitch which is different from that of a second section 52 of the screw passing through the intermediate leg 14. More particularly, the ratio of the pitch of the first screw section 50 to that of the second screw portion 52 equals the desired ratio of the distance L between the outer legs 12, 16 to the distance L' between the second outer leg 16 and the intermediate leg 14. In the case where such desired ratio is 3 to 1, for example, as the distance L between the outer legs 12, 16 increases a given amount, the intermediate leg 14 will be displaced away from the second leg 16 by one-third such given amount. As the distance L between the outer legs 12, 16 decreases by a given amount, the intermediate leg 14 will approach the second leg 16 by one-third such given amount.

Figure 2:
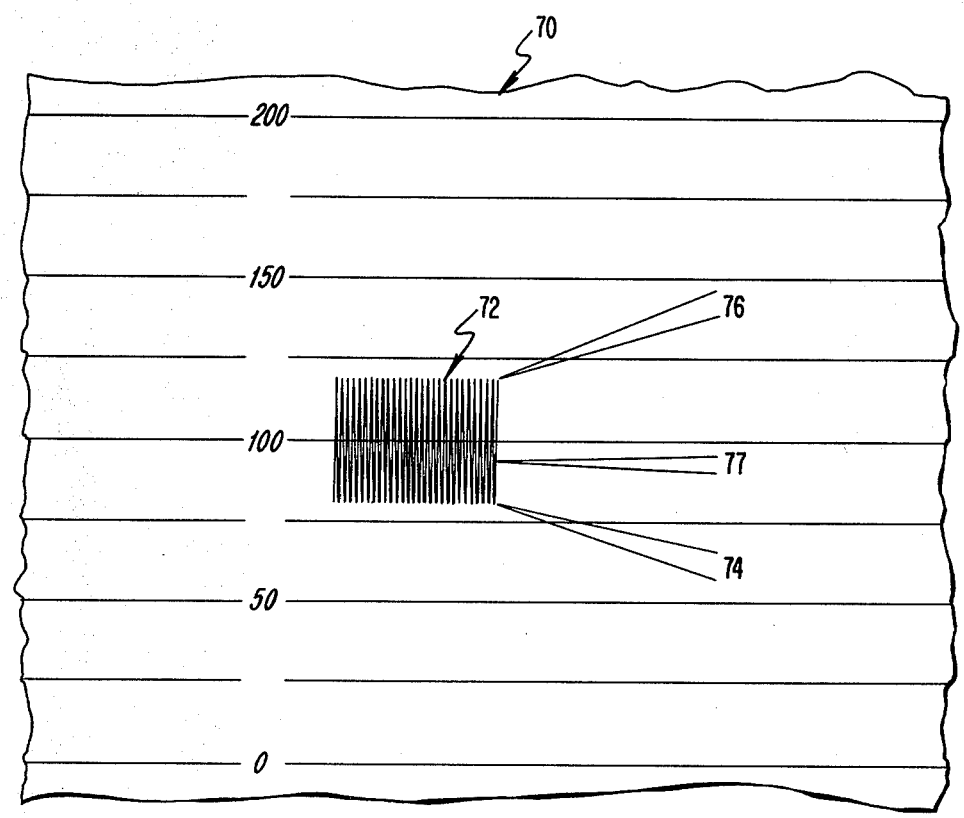

In the case of measuring mean arterial pressure from a graph containing values of systolic pressure and diastolic pressure, the adjusting mechanism constantly maintains the outer end 56 of the intermediate leg 14 one-third the distance between the outer ends 58, 60 of the outer legs. This is preferably accomplished by employing a first screw 50 section having a pitch of 1/24 and a second screw section 52 having a pitch of 1/72. The second outer leg 16 may be termed the "reference" leg and the first outer leg 12 may be termed the "excursion" leg. In FIG. 2 there is depicted a chart 70, such as a polygraph chart, a Z-fold paper chart or an oscilloscope screen which contains a graph 72 having a value of systolic pressure (maximum reading) and a value of diastolic pressure (minimum reading). To obtain a reading of mean arterial pressure directly from the graph, the instrument 10 may be positioned such that the outer end 60 of the reference leg 16 lies on a value 74 of diastolic pressure. Then, the adjustment knob 44 is rotated to extend (or retract) the excursion leg 12 until the outer end 58 of the excursion leg 12 lies on the corresponding value 76 of systolic pressure. Since the outer end 56 of the intermediate leg 14 has, during such adjustment, been maintained at one-third the distance from the outer end 60 of the reference leg 16 to the outer end 58 of the excursion leg 12, the outer end 56 of the intermediate leg 14 will indicate a value 76 on the graph which is located one-third the distance from the diastolic pressure value 74 to the systolic pressure value 76 and which thus constitutes the value of mean arterial pressure. It will be appreciated that only one reading from the graph is required, as opposed to the plurality of readings and calculations heretofore needed.

It will be understood that the instrument 10 can also be operated by initially placing the excursion leg 12 on the value of systolic pressure 76 and thereafter adjusting the screw, whereupon the reference leg 16 will be displaced toward the value of diastolic pressure.

Moreover, the adjusting screw 42 can be made to threadedly engage both of the outer legs, rather than just one. In this regard, if screw sections contacting the outer legs are made identical, each having a pitch of 1/24, then it will be appreciated that the outer legs will converge (or diverge) at twice the rate per screw revolution than in the afore-described case where the screw threadedly engages only one of the outer legs. Accordingly, it would be necessary to double the pitch of the screw section which engages the intermediate leg (i.e., to provide a pitch of 1/36) in order to constantly maintain the one-third ratio.

Of course, other variations of the invention are possible. For example, the control knob 44 need not be positioned exteriorly of the outer legs 12, 16, but could be located therebetween.

Although the invention has been described in connection with a preferred embodiment thereof, it will be appreciated by those skilled in the art that additions, substitutions, deletions, modifications not specifically described may be made without departing from the spirit and scope of the invention as defined in the appended claims.

What is claimed is:

1. A measuring instrument comprising first and second outer legs, a single intermediate leg disposed therebetween, said outer legs being arranged to pivot about a common axis to enable the distance between outer ends thereof to be manually varied, means for preventing movement of said intermediate leg in a direction parallel to the common pivot axis of said outer legs, proportioning means for maintaining an outer end of said intermediate leg at a constant ratio of the distance between said outer legs, said proportioning means including a manual adjusting screw having a first end rotatably supported by one of the outer legs and having a first section threadedly connected to the other of said outer legs to vary the distance between said outer legs upon being rotated, and a second section threadedly engaging said intermediate leg, the pitch of said first section being different from that of said second section and the ratio between the pitches being the same as said constant ratio.

2. A measuring instrument according to claim 1, wherein said first screw section is threadedly connected to only one of said outer legs, said first screw section having a pitch of 1/24 and said second screw section having a pitch of 1/72 so that said outer end of said intermediate leg is constantly maintained at a location one-third the distance between said outer ends of said outer legs.

3. A measuring instrument comprising first and second outer legs, a single intermediate leg disposed therebetween, said outer legs being arranged to enable the distance between outer ends thereof to be manually varied, proportioning means for maintaining an outer end of said intermediate leg at a constant ratio of the distance between said outer legs, said outer legs being connected at their upper ends for rotation about a common axis, said intermediate leg being mounted for rotation about said axis, a manual adjusting screw being provided for varying the spacing between said outer legs and for defining said proportioning means, and a control knob connected to said screw for rotating the latter, said screw having a first end rotatably supported by one of the outer legs and having a first threaded section threadedly engaging the other of said outer legs and a second threaded section threadedly engaging said intermediate leg, said first and second threaded sections being of different pitch.

4. A measuring instrument for determining the mean arterial blood pressure from a graph containing values of systolic pressure and diastolic pressure, said instrument comprising a compass having a pair of outer legs and a single intermediate leg disposed therebetween, said outer legs being arranged to pivot about a common axis to enable the distance between outer ends thereof to be manually varied, means for preventing movement of said intermediate leg in a direction parallel to the common axis of said outer legs, and proportioning means for maintaining an outer end of said intermediate leg at a constant ratio of the distance between said outer legs, said proportioning means including a manual adjusting screw having a first end rotatably supported by one of the outer legs and having a first section threadedly engaging the other of said outer legs to vary the distance between said outer legs upon being rotated, and a second section threadedly engaging said intermediate leg, the pitch of said first section being three times that of said second section such that said adjusting screw constantly maintains said intermediate leg at a location one-third the distance between said outer legs.

5. A measuring instrument according to claim 4, wherein said first screw section threadedly engages only one of said outer legs, said first screw section having a pitch of 1/24 and said second screw section having a pitch of 1/72.

6. A measuring instrument for determining the mean arterial blood pressure from a graph containing values of systolic pressure and diastolic pressure, said instrument comprising a compass having a pair of outer legs and a single intermediate leg disposed therebetween, said outer legs being arranged to enable the distance between outer ends thereof to be manually varied, proportioning means for maintaining an outer end of said intermediate leg at a constant ratio of one-third the distance between said outer legs, said outer legs being connected at their upper ends for rotation about a common axis, said intermediate leg being mounted for rotation about said axis, a manual adjusting screw being provided for varying the spacing between said outer legs and for defining said proportioning means, and a control knob connected to said screw for rotating the latter, said screw having a first end rotatably supported by one of the outer legs and having a first threaded section threadedly engaging the other of said outer legs and a second threaded section threadedly engaging said intermediate leg, said first and second threaded sections being of different pitch.

* * * * *